USOO5663335A

United States Patent [19]
Qi et al.

[11] Patent Number: 5,663,335
[45] Date of Patent: Sep. 2, 1997

[54] IMMUNOSUPPRESSIVE COMPOUNDS AND METHODS

[75] Inventors: You Mao Qi, Los Altos; John H. Musser, San Carlos, both of Calif.

[73] Assignee: Pharmagenesis, Inc., Palo Alto, Calif.

[21] Appl. No.: 609,277

[22] Filed: Mar. 1, 1996

[51] Int. Cl.$^6$ .................................................. C07D 295/04
[52] U.S. Cl. ........................... 544/153; 548/525; 549/297
[58] Field of Search ........................... 549/297; 514/468; 544/153; 548/525

[56] References Cited

U.S. PATENT DOCUMENTS

| | | | |
|---|---|---|---|
| 4,005,108 | 1/1977 | Kupchan et al. | 549/297 |
| 5,294,443 | 3/1994 | Lipsky et al. | 514/468 |
| 5,430,054 | 7/1995 | Qian et al. | 549/297 |

FOREIGN PATENT DOCUMENTS

| | | | |
|---|---|---|---|
| 1052859A | 7/1991 | China | 514/468 |
| 3178977A | 9/1989 | Japan | 514/468 |

OTHER PUBLICATIONS

Briggs, J.D., "A Critical Review of Immunosuppressive Therapy," *Immunol. Let.* 29:89–94 (1991).

Chen, K. et al., "Anti-AIDS Agents, 4. Tripteriforidin, a Novel Anti-HIV Principle from Tripterygium wilfordii: Isolation and Structural Elucidation," *J. Natl. Prod.* 55(1):88–92 (1992).

Huying, S. et al., "Effects of Tripterygium wilfordii on the Menstruation of 50 Patients Suffering from Rheumatoid Arthritis—with a Summary of its Therapeutic Effects in 12 Cases of Menorrhagia," *J. Trad. Chin. Med.* 4(3):237–240 (1984).

Juling, G. et al., "Tripterygium wilfordii Hook f in Rheumatoid Arthritis and Ankylosing Spondylitis," *Chin. Med. J.* 94(7):405–412 (1981).

Keown, P.A., "Annual Review of Transplantation" from *Clinical Transplants* (Terasaki, P., Ed.), UCLA Tissue Typing Laboratory, Los Angeles, California, pp. 205–223 (1991).

Kupchan, S.M. et al., "Triptolide and Tripdiolide, Novel Antileukemic Diterpenoid Tripoxides from Tripterygium wilfordii," *J. Am. Chem. Soc.* 94(2):7194–7195 (1972).

Li, X.W., and Weir, M.R., "Radix Tripterygium wilfordii—a Chinese Herbal medicine with Potent Immunosuppressive Properties," *Transplantation* 50(1):82–86 (1990).

Ma, P.C. et al., "16–Hydroxtriptolide, an Active Diterpene Isolated from Tripterygium Wilfordii," *Acta Pharma Sinica* 26:759–763 (1991).

Ma, P.C. et al., "16–Hydroxtriptolide, an Active Compound from Tripterygium wilfordii," *J. Chinese Pharm.* 1(2):12–18 (1992).

Ma, P.C. et al., "16–Hydroxtriptolide, a New Active Diterpene Isolated from Tripterygium wilford H.," *Chem. Abstracts* 116:143775f (1992).

Meifang, C. et al., "Treatment of Chronic Nephritis with Tripterygium Hypoglaucum," *J. Trad. Chin. Med.* 3(3):219–222 (1983).

Yang, S.X. et al., "Immunosuppression of Triptolide and its Effects on Skin Allograft Survival," *Int. J. Immunopharmac.* 14(6):963–969 (1992).

Zheng, J. et al., "Screening of Active Anti–Inflammatory, Immunosuppressive and Antifertility Components of Tripterygium wilfordii," *Zhongguo Yixue Kexyeyuan Xuebao* 13(6):391–398 (1991).

Zheng, J. et al., "Screening of Anti–Inflammatory, Immunosuppressive and Antifertility Components of Tripterygium wilfordii," *Zhongguo Yixue Kexyeyuan Xuebao* 16(1):24–28 (1994).

Burger, "A Guide to the Chemical Basis of Drug Design", pp. 82–87 (1984).

*Primary Examiner*—James H. Reamer
*Attorney, Agent, or Firm*—Vincent M. Powers; LeeAnn Gorthey

[57] ABSTRACT

Compounds and methods for use in immunosuppressive and anti-inflammatory treatment are described. The compounds are triptolide analogs with improved water solubility and low toxicity.

19 Claims, 7 Drawing Sheets

IMMUNOSUPPRESSIVE COMPOUNDS AND METHODS

FIELD OF THE INVENTION

The present invention relates to compounds and methods for use in immunosuppressive and anti-inflammatory treatment.

References
Bradley, L., in SELECTED METHODS IN CELLULAR IMMUNOLOGY, W. H. Freeman and Company, San Francisco, pp. 162–164 (1980).
Briggs, J. D., Immunol. Lett. 29(1–2):89–94 (1991).
Hasan, R., et al., Transplantation 54:408 (1992).
Kennedy, M. S., et al., Am. J. Med. 78:978 (1983).
Keown, P. A., Clin. Transplants 205–223 (1991).
Kocienski, P. J., PROTECTING GROUPS, Georg Thieme Verlag, Stuttgart (1994).
Kupchan, S. M., et al., J. Am. Chem. Soc. 94:7194 (1972).
Kupchan, S. M., et al., U.S. Pat. No. 4,005,108 (1977).
Lipsky, P. E., et al., U.S. Pat. No. 5,294,443 (1994).
Ma, P.-C., et al., J. Chin. Pharm. Sci. 1:12 (1992).
Mishell, B., et al., Eds., in SELECTED METHODS IN CELLULAR IMMUNOLOGY W. H. Freeman and Co., San Francisco, Calif. (1980).
Morris, R. E., Transplant Proc. 23(6):2722–2724 (1991).
Morris, R. E., et al., Transplant Proc. 23(1):238–240 (1991).
Mossmann, T., J. of Immunological Methods 65:55 (1983).
Murase, N., et al., Transplantation 55:701 (1993).
O'Gara, A., and Defrance, T., in LABORATORY METHODS IN IMMUNOLOGY, Zola, H., Ed., CRC Press (1990).
Ono and Lindsey, J. Thor. Cardiovasc. Surg. 57(2):225–29 (1969).
Platt, J. L., et al., Immunology Today 11(12):450 (1990).
Pu, L., et al., Zhongguo Yaoli Xuebao 11:76 (1990).
Roberts, J. P., et al., Ann. Rev. Med. 40:287 (1989).
Schumacher, H. R., Ed., in PRIMER ON THE RHEUMATIC DISEASES, Ninth Ed., Arthritis Foundation, Atlanta, Ga. (1988).
Storb, R., "Pathophysiology and Prevention of Graft-Versus-Host Disease," in ADVANCES IN IMMUNOBIOLOGY: BLOOD CELL ANTIGENS AND BONE MARROW TRANSPLANTION, McCullogh, J., and Sandler, S. G., Editors, Alan R. Liss, Inc., New York, p. 337 (1984).
Storb, R., Blood 66:698 (1985).
Storb, R., et al., N. Engl. J. Med. 314:729 (1986).
Thomas, E. D., et al., N. Engl. J. Med. 292:832 (1975).
Wang, J., and Morris, R. E., Transplantation Proc. 23:699 (1991).
Weiden, P. L., et al., "Graft-Versus-Host Disease in Allogeneic Marrow Transplantation," in BIOLOGY OF BONE-MARROW TRANSPLANTATION, Gale, R. P. and Fox, C. F., Eds., Academic Press, New York, p. 37 (1980).
Zheng, J., et al., ZHONGGUO YIXUE KEXUEYUAN XUE-BAO 3:391 (1991).
Zheng, J., et al., ZHONGGUO YIXUE KEXUEYUAN XUE-BAO 16:24 (1994).

BACKGROUND OF THE INVENTION

The immune system functions as the body's major defense against diseases caused by invading organisms. This complex system fights disease by killing invaders such as bacteria, viruses, parasites or cancerous cells while leaving the body's normal tissues unharmed. The immune system's ability to distinguish the body's normal tissues, or self, from foreign or cancerous tissue, or non-self, is an essential feature of normal immune system function. A second essential feature is memory, the ability to remember a particular foreign invader and to mount an enhanced defensive response when the previously encountered invader returns. The loss of recognition of a particular tissue as self and the subsequent immune response directed against that tissue produce serious illness.

An autoimmune disease results from the immune system attacking the body's own organs or tissues, producing a clinical condition associated with the destruction of that tissue. An autoimmune attack directed against the joint lining tissue results in rheumatoid arthritis; an attack against the conducting fibers of the nervous system results in multiple sclerosis. The autoimmune diseases most likely share a common pathogenesis and the need for safe and effective therapy.

Rheumatoid arthritis is one of the most common of the autoimmune diseases. Current treatments utilize three general classes of drugs (Schumacher, 1988): antiinflammatory agents (aspirin, non-steroidal anti-inflammatory drugs and low dose corticosteroids); disease-modifying antirheumatic drugs, known as "DMARDs" (antimalarials, gold salts, penicillamine, and sulfasalazine) and immunosuppressive agents (azathioprine, chlorambucil, high dose corticosteroids, cyclophosphamide, methotrexate, nitrogen mustard, 6-mercaptopurine, vincristine, hydroxyurea, and cyclosporin A). None of the available drugs are completely effective, and most are limited by severe toxicity.

In addition to their use in treating autoimmune conditions, immunosuppressive agents have also been used in treating or preventing transplantation rejection. Organ transplantation involving human organ donors and human recipients (allografts), and non-human primate donors and human recipients (xenografts), has received considerable medical and scientific attention (Roberts, 1989; Platt, 1990; Keown, 1991; Wang and Morris, 1991; Hasan, 1992; Murase, 1993). To a great extent, these efforts has been aimed at eliminating, or at least reducing, the problem of rejection of the transplanted organ. In the absence of adequate immunosuppressive therapy, the transplanted organ is destroyed by the host immune system.

Another obstacle in transplantation, which has limited bone marrow transplants (BMT) in particular, is graft-versus-host disease (GVHD). GVHD is a condition in which transplanted marrow cells attack the recipient's cells (Thomas, 1975; Storb, 1984). Many BMT patients receiving HLA-identical marrow that tests negative in the mixed lymphocyte reaction (MLR) still develop GVHD, presumably because of a disparity between the recipient and donor at polymorphic non-HLA determinants. A large proportion of GVHD-afflicted individuals die as a result of GVHD (Weiden, et al., 1980).

Presently, the most commonly used agents for preventing transplant rejection include corticosteroids, antimetabolite drugs that reduce lymphocyte proliferation by inhibiting DNA and RNA synthesis such as azathioprine, immunosuppressive drugs such as cyclosporin A, which specifically inhibits T cell activation, and specific antibodies directed against T lymphocytes or surface receptors that mediate their activation (Briggs, 1991; Kennedy, 1983; Storb, 1985; Storb, et al., 1986). All of these drug therapies are limited in effectiveness, in part because the doses needed for effective treatment of transplant rejection may increase the patient's susceptibility to infection by a variety of opportunistic invaders, and in part because of direct toxicity and other side effects. For example, cyclosporin A, currently the most commonly used agent, is significantly toxic to the kidney. This nephrotoxicity limits the quantity of drug that can be safely given.

Recently, a number of compounds from the Chinese medicinal plant *Tripterygium Wilfordii* (TW) have been identified as having immunosuppressive activity. Representative compounds which have been isolated from TW include triptolide, 16-hydroxytriptolide, triptophenolide, tripdiolide, and celastrol, as described for example in Lipsky, et al. (1994) and Zheng et al. (1991; 1994). However, the administration and therapeutic effectiveness of these compounds have been limited by their low water solubility.

One approach for improving the effectiveness of these compounds is to formulate them in mixtures of ethanol and polyethoxylated castor oil (e.g., "CREMOPHOR EL"), allowing subsequent dilution in saline for intravenous administration. However, such formulations have suffered from high toxicity, due to the high concentration of solubilizing agent required to dissolve these compounds. For example, the ratio of solubilizing agent (ethanol plus "CREMOPHOR EL") to triptolide in such formulations is typically on the order of 1000:1 or greater, due to the poor solubility of triptolide (Morris, 1991; Morris, et al., 1991). Standardization of dosage amounts is also more problematic with a suspension than with a solution.

It would therefore be desirable to provide immunosuppressive compounds having improved water solubility and low toxicity. In addition, it would be desirable for such compounds to exhibit immunosuppressive activity in their water soluble form, or to be convertible to an immunosuppressive form by metabolic processes in vivo.

SUMMARY OF THE INVENTION

The invention includes, in one aspect, a compound having the structure represented by Formula 1 below, wherein $X^1$ is OH or $OR^1$, and $X^2$ and $X^3$ are independently OH, $OR^1$ or H, with the proviso that at least one of $X^2$, $X^2$ and $X^3$ is $OR^1$, and at least one of $X^2$ and $X^3$ is H; and $R^1$ is —C(O)—Y—Z, wherein Y is a branched or unbranched $C_1$–$C_6$ alkyl or alkenyl chain; and Z is $COOR^2$, $NR^3R^{3'}$, or $^+NR^4R^{4'}R^{4''}$, where $R^2$ is a cation; $R^3$ and $R^{3'}$ are independently H or branched or unbranched $C_1$–$C_6$ alkyl, hydroxyalkyl, or alkoxyalkyl, or, taken together, form a 5- to 7-member heteroatom ring containing 2 to 6 carbon atoms; and $R^4$, $R^{4'}$, and $R^{4''}$ are independently branched or unbranched $C_1$–$C_6$ alkyl, hydroxyalkyl or alkoxyalkyl.

In one general embodiment, the compound is a derivative of triptolide, wherein $X_1$ is OH or $OR_1$ as defined above, and $X^2$ and $X^3$ are H. In a second general embodiment, the compound is a derivative of 16-hydroxyl triptolide, wherein $X_1$ and $X_3$ are OH or $OR_1$, and $X_2$ is H. In a third general embodiment, the compound is a derivative of tripdiolide (2-hydroxytriptolide), wherein $X_1$ and $X_2$ are OH or $R_1$, and $X^3$ is H.

In one preferred embodiment, Z is COOH or $COOR^2$, where $R^2$ is a metal ion, preferably $Na^+$ or $K^+$. In an alternative embodiment, $R^2$ is a positively charged amine, preferably lysine, triethylamine, or tris(hydroxymethyl) aminomethane. Preferably, $R^2$ is $Na^+$, tris(hydroxymethyl) aminomethane or lysine, and Y is a $C_1$–$C_4$ alkyl chain.

In another preferred embodiment, Z is $NR^3R^{3'}$, where $R^3$ and $R^{3'}$ are independently H or branched or unbranched $C_1$–$C_6$ alkyl, or together form a 5- to 7-member heteroatom ring containing 2 to 6 carbon atoms. Preferably, Z is dimethyl amino, diethyl amino, or N-morpholino, and Y is a $C_1$–$C_4$ alkyl chain.

Where Z is a quaternary or protonated tertiary amino group, the compound also includes an anionic counterion. The anionic counterion is preferably a halide or a carboxylate-, sulfonate-, or sulfate-containing ion. More preferably, the counterion is chloride, bromide, acetate, oxalate, maleate, fumarate, methanesulfonate, or toluenesulfonate.

In another aspect, the invention includes a pharmaceutical composition for immunosuppressive treatment. The composition includes a compound in accordance with Formula 1 above, in a pharmaceutically acceptable vehicle. In a preferred embodiment, the vehicle is an aqueous carrier.

In another aspect, the invention includes an immunosuppressive treatment method wherein a composition as described above is administered to a subject in need of such treatment. The method is useful for inhibiting allograft rejection, xenograft rejection, and graft-versus-host disease, and in treating autoimmune diseases such as rheumatoid arthritis.

The compositions and method of the invention are also useful for the treatment of asthma, both intrinsic and extrinsic manifestations. For treatment of asthma, the composition is preferably administered via inhalation.

The composition and method may also be used for treatment of other inflammatory conditions, such as traumatic inflammation, including traumatic inflammation accompanying head or neck injury.

These and other objects and features of the invention will become more fully apparent when the following detailed description of the invention is read in conjunction with the accompanying drawings.

DETAILED DESCRIPTION OF THE INVENTION

I. Definitions

The terms below have the following meanings unless indicated otherwise.

"Triptolide derivatives" or "triptolide analogs" refers to derivatives of triptolide, 16-hydroxytriptolide and tripdiolide (2-hydroxytriptolide) which are derivatized at one or more hydroxyl groups as described above.

"Alkyl" refers to a fully saturated monovalent or divalent radical containing carbon and hydrogen, and which may be cyclic, branched or a straight (unbranched) chain. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl, and cyclohexyl.

"Lower alkyl" refers to an alkyl radical of one to four carbon atoms, as exemplified by methyl, ethyl, n-propyl, i-propyl, n-butyl, i-butyl, and t-butyl.

"Alkenyl" refers to a monovalent or divalent unsaturated, preferably mono-unsaturated, radical containing carbon and hydrogen, and which may be cyclic, branched or a straight chain.

"Heteroatom" refers to carbon, nitrogen, oxygen, or sulfur."

"A 5- to 7-member heteroatom ring containing 2 to 6 carbon atoms" refers to a heterocyclic ring whose chain atoms include one or more nitrogen atoms and, optionally, one or more oxygen or sulfur atoms. Examples are piperidine, piperazine, morpholine, and pyrrolidine.

"Alkoxyalkyl" refers to an alkyl group as defined above, additionally containing an alkoxy substituent. Preferably, the alkyl portion of the alkyloxy substituent is a lower alkyl group.

For the purpose of the current disclosure, the following numbering scheme is used for triptolide and triptolide analogs:

II. Synthesis of Triptolide Analogs

This section describes the synthesis of compounds in accordance with the present invention as defined by Formula 1 above. In general, the compounds are ester derivatives of triptolide, tripdiolide or 16-hydroxytriptolide, wherein the attached ester substituents include one or more amino or carboxylate groups. The compounds possess greater water solubility than do the non-derivatized starting compounds and are useful as prodrugs for immunosuppressive and anti-inflammatory applications.

The compounds of the invention may be prepared from triptolide, tripdiolide, or 16-hydroxytriptolide obtained from the root xylem of the Chinese medicinal plant *Tripterygium Wilfordii* (TW) or from other known sources. The TW plant is found in the Fujiang Province and other southern provinces of China; TW plant material can generally be obtained in China or through commercial sources in the United States. Methods for preparing triptolide, tripdiolide, and 16-hydroxytriptolide are known in the art and are described, for example, in Kupchan, et al. (1972); Kupchan, et al. (1977); Lipsky, et al. (1994); Pu, et al. (1990); and Ma, et al. (1992).

Figure 1:
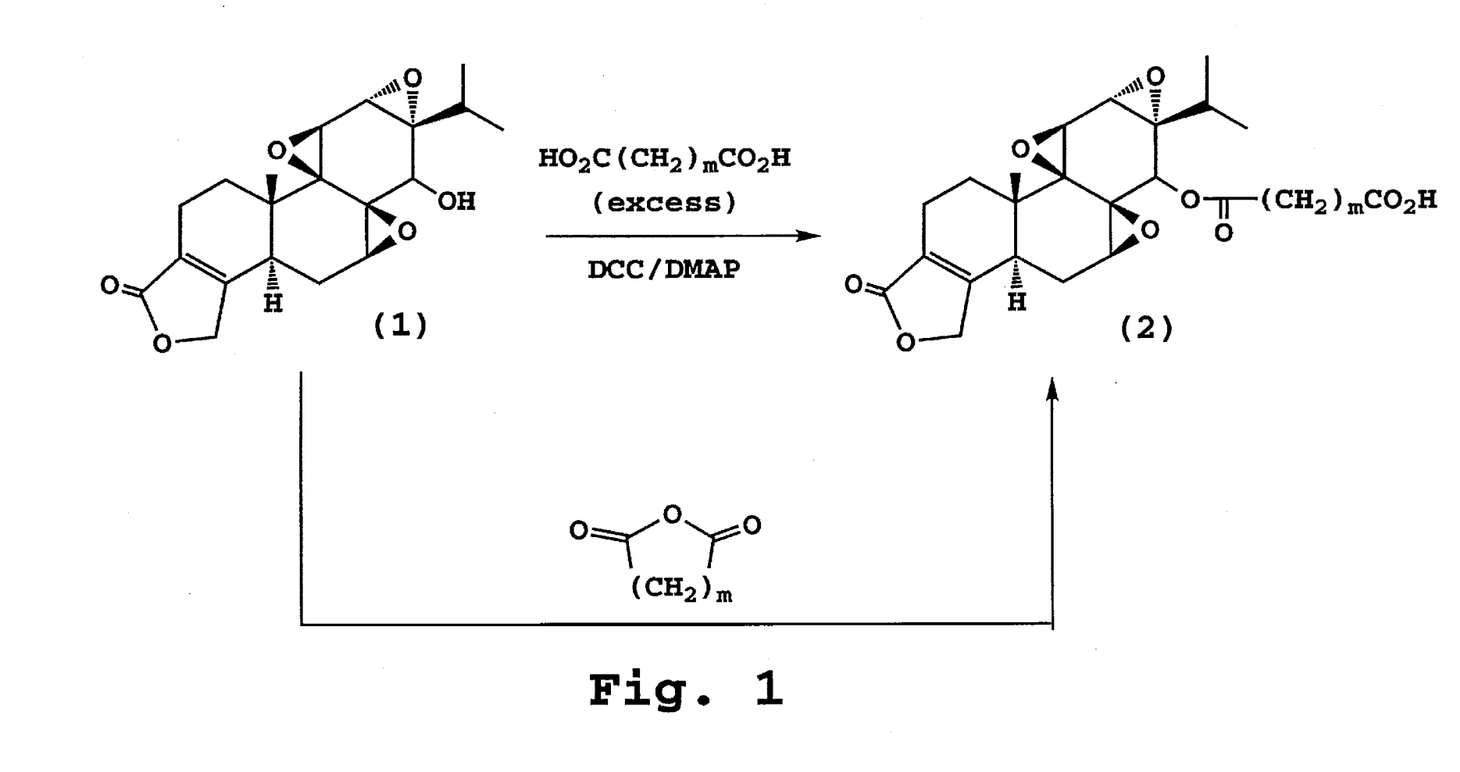
FIG. 1 shows a scheme for preparing a carboxylated triptolide compound in accordance with the invention.

Synthetic schemes for preparing carboxylated derivatives of triptolide in accordance with the invention are shown in FIG. 1. With reference to the upper reaction path shown in the figure, triptolide (1) is reacted with an excess of a dicarboxylic acid of the form $HO_2C(CH_2)_mCO_2H$, where m is 1 to 4, in the presence of a coupling agent such as dicyclohexylcarbodiimide (DCC) and a catalytic amount of an acylation catalyst such as 4-(dimethylamino)pyridine (DMAP). The reaction conditions are effective to activate one or both carboxylate groups in the dicarboxylic acid towards reaction with the 14-hydroxyl group of (1), such that ester product (2) is formed. Any residual DCC attached to the free carboxyl in (2) may be released by addition of water, preferably under basic conditions.

A second method for preparing carboxylated derivatives of (1) is shown in the lower reaction path in FIG. 1. In this approach, (1) is reacted with a selected dicarboxylic acid anhydride, under conditions effective for the 14-hydroxyl group of (1) to attack one of the anhydride carbonyl groups to produce product (2). Exemplary conditions for this approach can be found in Example 1.

More generally, the methods illustrated in FIG. 1 can be used to prepare triptolide derivatives in accordance with Formula 1 above, wherein $X_2$ and $X_3$ are H and $X_1$ is —C(O)—Y—Z (i.e., $R_1$ in Formula 1), wherein Y is a branched or unbranched $C_1$-$C_6$ alkyl or alkenyl chain, and Z is $COOR^2$, where $R^2$ is a cation.

Figure 2:
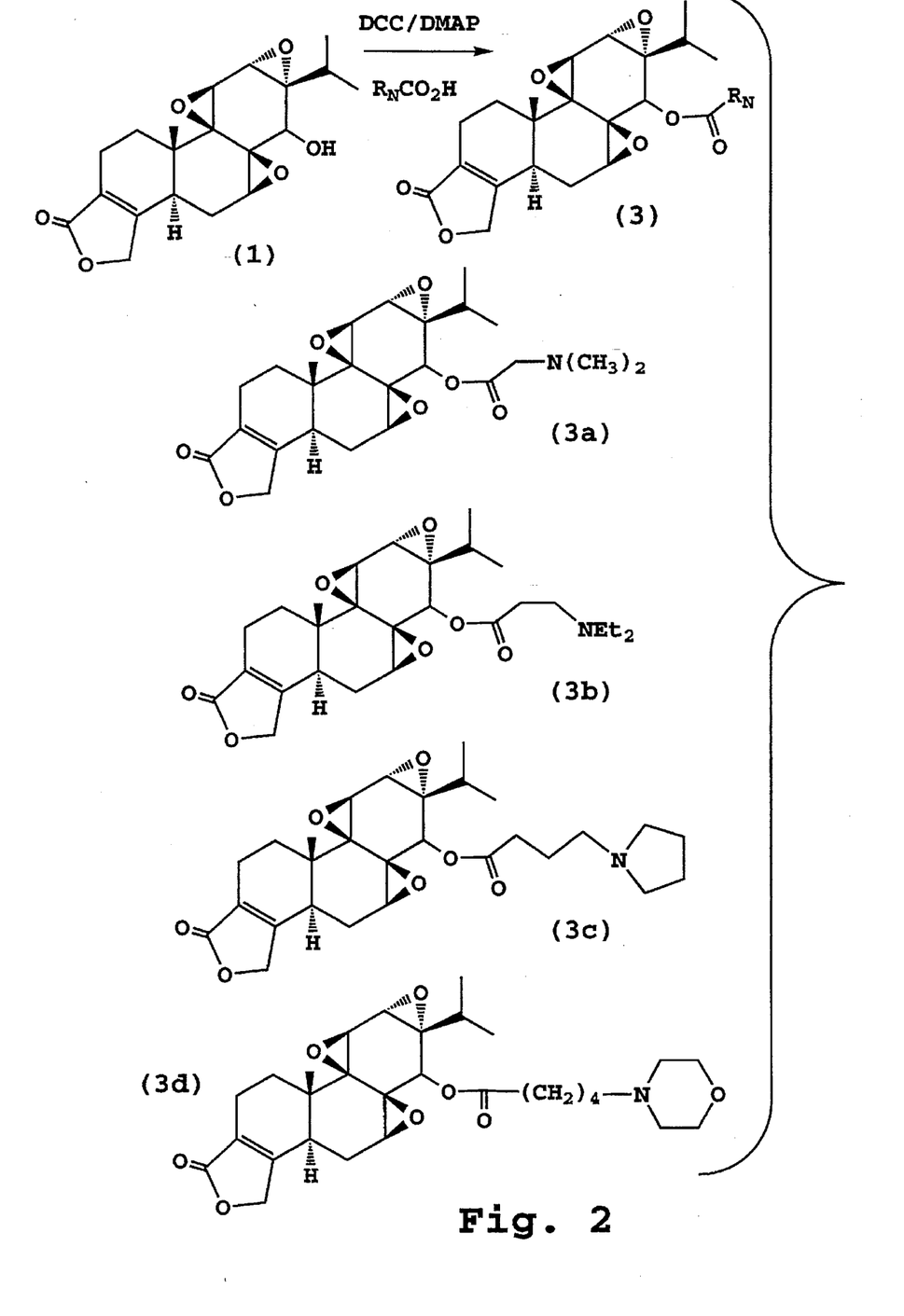
FIG. 2 shows a scheme for preparing amino derivatives of triptolide in accordance with the invention.

FIG. 2 illustrates a method for preparing aminoester derivatives of triptolide. Triptolide (1) is reacted with an amine-substituted carboxylic acid, $R_NCO_2H$, in the presence of a coupling agent (e.g. DCC) and an acylation catalyst (e.g. DMAP). These reaction conditions may be used to prepare a number of amino-derivatives, depending on the amino acid starting material. For example, reaction of (1) with N,N-dimethylglycine affords ester product (3a), as shown in FIG. 2 and described in Example 5. Similarly, reaction of (1) with 3-(N,N-diethylamino)propionic acid, 4-pyrrolidinobutyric acid, or 5-morpholinopentanoic acid affords product (3b), (3c), or (3d), respectively, as detailed in Examples 7–9. Amine salts in accordance with the invention are readily prepared by treatment with a selected acid, as in Example 6, or by using an ammonium salt form of $R_NCO_2H$ in the coupling step, as in Examples 7 and 8.

Thus, it will be seen that the approach in FIG. 2 may be used to prepare amino-derivatives in accordance with structure (3) in FIG. 2, wherein $R_N$ has the form Y—Z as defined in the Summary of the invention. Y is a branched or unbranched $C_1$-$C_6$ alkyl or alkenyl chain, Z is $NR^3R^{3'}$ or $^+NR^4R^{4'}R^{4''}$, $R^3$ and $R^{3'}$ are independently H or branched or unbranched $C_1$-$C_6$ alkyl, hydroxyalkyl, or alkoxyalkyl, or, taken together, form a 5- to 7-member heteroatom ring containing 2 to 6 carbon atoms, and $R^4$, $R^{4'}$, and $R^{4''}$ are independently branched or unbranched $C_1$-$C_6$ alkyl, hydroxyalkyl or alkoxyalkyl. In the case where Z is $NR^3R^{3'}$ where $R^3$ and $R^{3'}$ together form a ring, preferred ring moieties include morpholine, piperidine, pyrrolidine, and piperazine.

Moreover, while FIGS. 1 and 2 illustrate reaction schemes using triptolide as the starting material, it will be appreciated that similar synthetic reaction schemes can be used to prepare corresponding ester derivatives of 16-hydroxytriptolide and tripdiolide.

Figure 3:
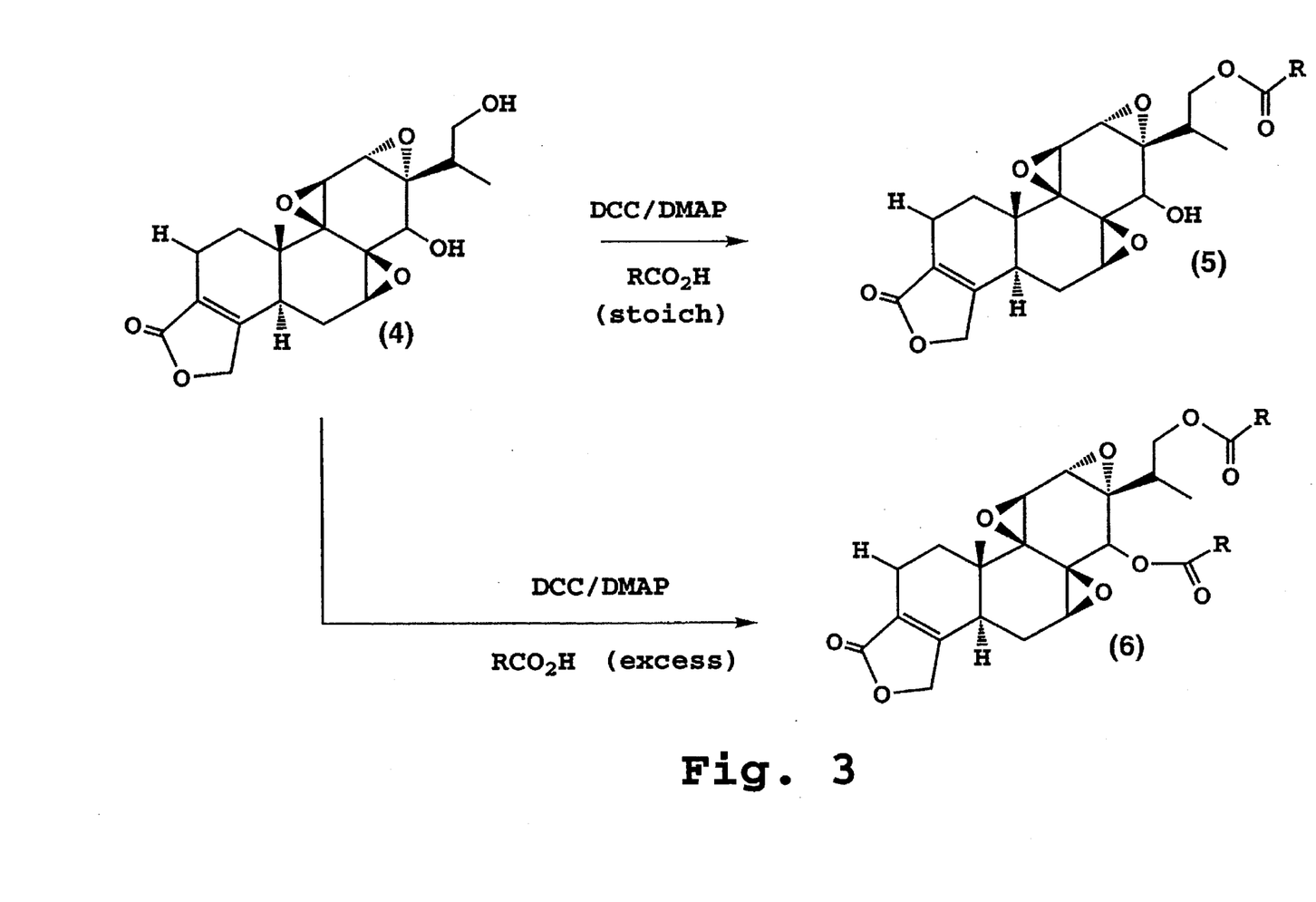
FIG. 3 shows a scheme for preparing mono- and diaminoester derivatives of 16-hydroxytriptolide.

FIG. 3 illustrates synthetic approaches for preparing mono- and diester derivatives of 16-hydroxytriptolide (4), a compound which contains two free hydroxyl groups. As can be seen from the figure, compound (4) contains a hydroxyl group at the 14-position which is linked to a secondary carbon atom, and a second hydroxyl group at the 16-position which is linked to a primary carbon atom. Since the hydroxyl group at the 16-position is more reactive than the 14-hydroxyl group for steric reasons, mono- and diester derivatives can be selectively made using appropriate reaction conditions.

As shown in the upper reaction path of FIG. 3, reaction of (4) with a stoichiometric amount of a selected carboxylic acid yields monoester (5) derivatized at the 16-position, with the 14-hydroxyl group remaining free. Conversely, as shown in the lower reaction path, reaction of (4) with an excess of the carboxylic acid is effective to derivatize both hydroxyl groups, affording diester (6).

Figure 4:
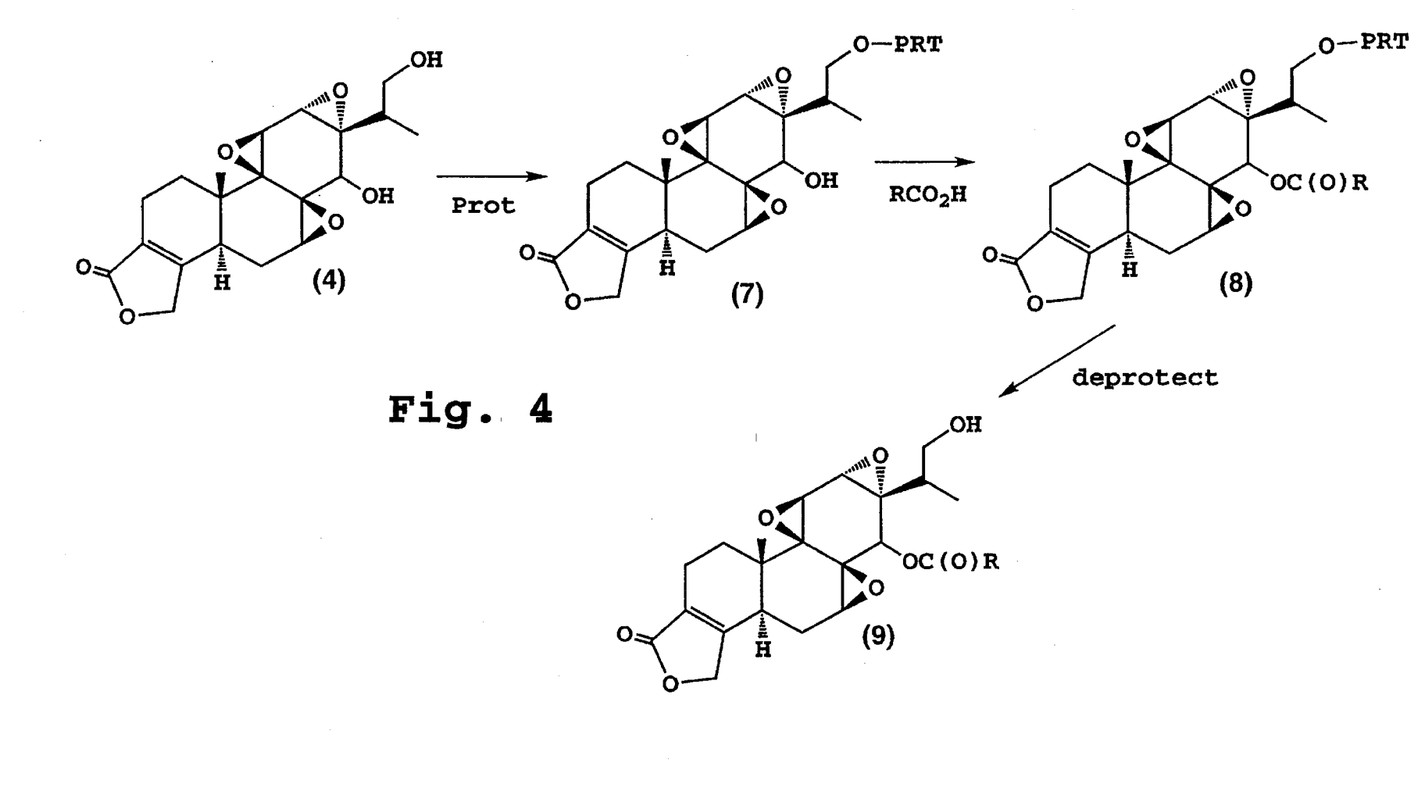
FIG. 4 shows a scheme for preparing a 14-aminoester derivative of 16-hydroxytriptolide by means of protection and deprotection of the 16-hydroxyl group.

Monoester derivatives of 16-hydroxytriptolide (4) at the 14-position, rather than the 16-position, can be prepared by the general approach shown in FIG. 4. This approach takes advantage of the greater reactivity of the 16-hydroxyl group towards electrophiles, whereby the 16-hydroxyl can be selectively protected with a protecting group (PRT), as shown in the first step of FIG. 4. The protected compound (7) is then reacted with a selected carboxylic acid ($RCO_2H$) to esterify the 14-hydroxyl group, forming compound (8). The protecting group is then removed in a deprotection, to yield the desired 14-monoester (9). Suitable hydroxyl protecting groups for the purposes of the protection/deprotection scheme in FIG. 4 are known, and are described, for example, by Kocienski (1994). One preferred protecting group is a benzyl ether, which may be removed by catalytic hydrogenation (Kocienski, 1994, p. 46). Alternatively, a t-butyldimethyl silyl ether may be used. This group can be removed by, e.g., treatment with tetrabutyl ammonium fluoride (TBAF).

Selective single derivatization of tripdiolide (2-hydroxytriptolide) is more difficult because of the similar reactivities of the two secondary hydroxyls. Accordingly, the 2- and 14-monoesters may be prepared as a mixture either by (1) reacting tripdiolide with a comparable amount of carboxylic acid (e.g., 1 to 3 equivalents) or (2) briefly reacting tripdiolide with excess carboxylic acid followed quickly by addition of excess alcohol (e.g., ethanol) to quench the excess carboxylic acid. In either case, a mixture of mono- and diester forms can be obtained which may then be separated by standard chromatographic methods such as HPLC.

Metal salts and amine salts of the amino and carboxyl ester compounds of the invention are readily prepared by reaction or exchange with an appropriate counterion, as described in Examples 2–4 and 6. In the case of carboxyl ester compounds such as (2), suitable counterions include sodium and potassium ions, as well as organic amines such as mono, di, tri, or tetraalkyl amines wherein the alkyl groups are lower alkyl or alkoxy groups.

III. Stability of Triptolide Derivatives

Sodium triptolide succinate, designated YM-274, was dissolved in $D_2O$, and the aqueous solution was stored at room temperature. Proton NMR spectra were taken at intervals, as described in Example 10A, and showed the compound to be unchanged after three months in solution. After five months, some decomposition was observed.

The stability of triptolide succinate in blood serum was determined as detailed in Example 10B. In this study, a solution of triptolide succinate (YM-262, free acid) in DMSO was mixed with rat serum and incubated at 37° C. The mixture was assayed periodically by thin layer chromatography (TLC) to follow the hydrolysis of the triptolide succinate over time. Within the first 3 to 5 minutes, most of the triptolide succinate remained ($R_f$=0.45). After 15 minutes, the triptolide succinate spot was gone and a new spot corresponding to triptolide had appeared ($R_f$=0.60). Finally, after 45 minutes, the triptolide spot had also disappeared, and only low $R_f$ material (blood serum components and decomposition products) remained. These results indicate that the triptolide ester is hydrolyzed in serum to release free triptolide in less than an hour.

IV. Biological Activity

A number of succinate salt derivatives in accordance with the present invention were examined for immunosuppressive activity using several biological assays. The compounds tested were carboxylated esters of triptolide prepared by succinylation of triptolide followed by salt formation, as detailed in Examples 1 to 4, with the following designations: free acid, YM-262; tris(hydroxymethyl)aminomethane (tris) salt, YM-273; sodium salt, YM-274; and L-(+)-lysine salt, YM-276.

A. Inhibition of IL-1 Action

The ability of the above compounds to suppress the cell-proliferative effect of IL-1β (O'Gara, 1990) was examined as described in Example 11. Mouse thymocytes in culture were stimulated with IL-1β in the presence of phytohemagglutinin (PHA) and increasing concentrations of triptolide (control) and triptolide derivatives. The cells were cultured for 72 hours, and during the last 18 hours, incubated with tritiated thymidine. DNA synthesis was assessed by measuring incorporation of radiolabeled thymidine. The results expressed in terms of $IC_{50}$ (concentration effective to cause 50% suppression of proliferation) are shown in Table I.

TABLE I

| | IL-1 Assay | | |
|---|---|---|---|
| | $IC_{50}$ | | Toxicity |
| Compound | (ng/ml) | (nmol/ml) | (ng/ml) |
| Triptolide | 1.9 | 0.0053 | >12500 |
| YM-262 | 181 | 0.393 | >12500 |
| YM-273 | 462 | 0.8 | 12000 |
| YM-274 | 181 | 0.376 | >12500 |
| YM-276 | 144 | 0.238 | >12500 |

With reference to column 3 in Table I, triptolide showed an $IC_{50}$ value of about 0.005 nmol/ml, indicating that the free (underivatized) compound is a potent inhibitor of IL-1β action. In contrast, the free acid and salt forms of the triptolide 14-succinyl ester showed $IC_{50}$ values that were approximately 45- to 150-fold higher than that of free triptolide, indicating that the ester forms do not themselves possess significant immunosuppressive activity. On the other hand, all of the ester derivatives showed low cytotoxicity (Table II, column 4), as measured by MTT assay (Example 13).

B. Mixed Lymphocyte Reaction (MLR)

Inhibition of cell proliferation in the mixed lymphocyte reaction (MLR) (Bradley, 1980; Mishell, 1980) is a measure of in vivo immunosuppression. Spleen cells from female C57BL/6 mice, the "responder" cells, were prepared and co-cultured alone or in the presence of varying concentrations of the test compounds, with irradiated spleen cells prepared from female Balb/C mice, the "stimulator" cells. Prior irradiation of the stimulator cells rendered them unable to proliferate. A sample of the responder cells was also irradiated for use as a control. The non-irradiated responder cells proliferate in the presence of the allogenic stimulator cells. After a 78-hour incubation, tritiated thymidine was added to the mixed cell cultures, and incorporation of the labeled nucleotide into DNA was measured as an index of cell proliferation. The results are shown in Table II.

TABLE II

| Compound | MLR Assay | | Toxicity |
|---|---|---|---|
| | $IC_{50}$ | | |
| | (ng/ml) | (nmol/ml) | (ng/ml) |
| Triptolide | 0.9 | 0.0025 | 13.3 |
| YM-262 | 86 | 0.187 | 2258 |
| YM-273 | 180 | 0.31 | 5529 |
| YM-274 | 90 | 0.187 | 2498 |
| YM-276 | 63 | 0.104 | 1936 |

As can be seen, the data were qualitatively similar to those obtained with the IL-1 assay in Table I above, in that the free acid and salt forms of the triptolide 14-succinyl ester showed $IC_{50}$ values that were approximately 40- to 125-fold higher than that of free triptolide. Similarly, all of the ester derivatives showed low cytotoxicity, as measured by MTT assay (Example 13).

C. Cardiac Allograft Survival

Treatment of transplantation rejection, in accordance with the invention, is illustrated for rejection of an allograft by the heart transplantation model used in Example 14. The method involves a well-characterized rat model system (Oho and Lindsey, 1969) in which a transplanted heart is attached to the abdominal great vessels of an allogeneic recipient animal, and the viability of the transplanted heart is gauged by the heart's ability to beat in the recipient animal.

In one study, the animals were administered by intraperitoneal injections, from one day preceding to 14 days following heart transplantation, either control solution (5% ethanol, 10 ml/kg), triptolide (designated as T10), or with two concentrations each of YM-273 and YM-274. There were three animals in each group, except for the control group in which five animals were used. The results are shown in FIGS. 5A and 5B.

Figure 5A:
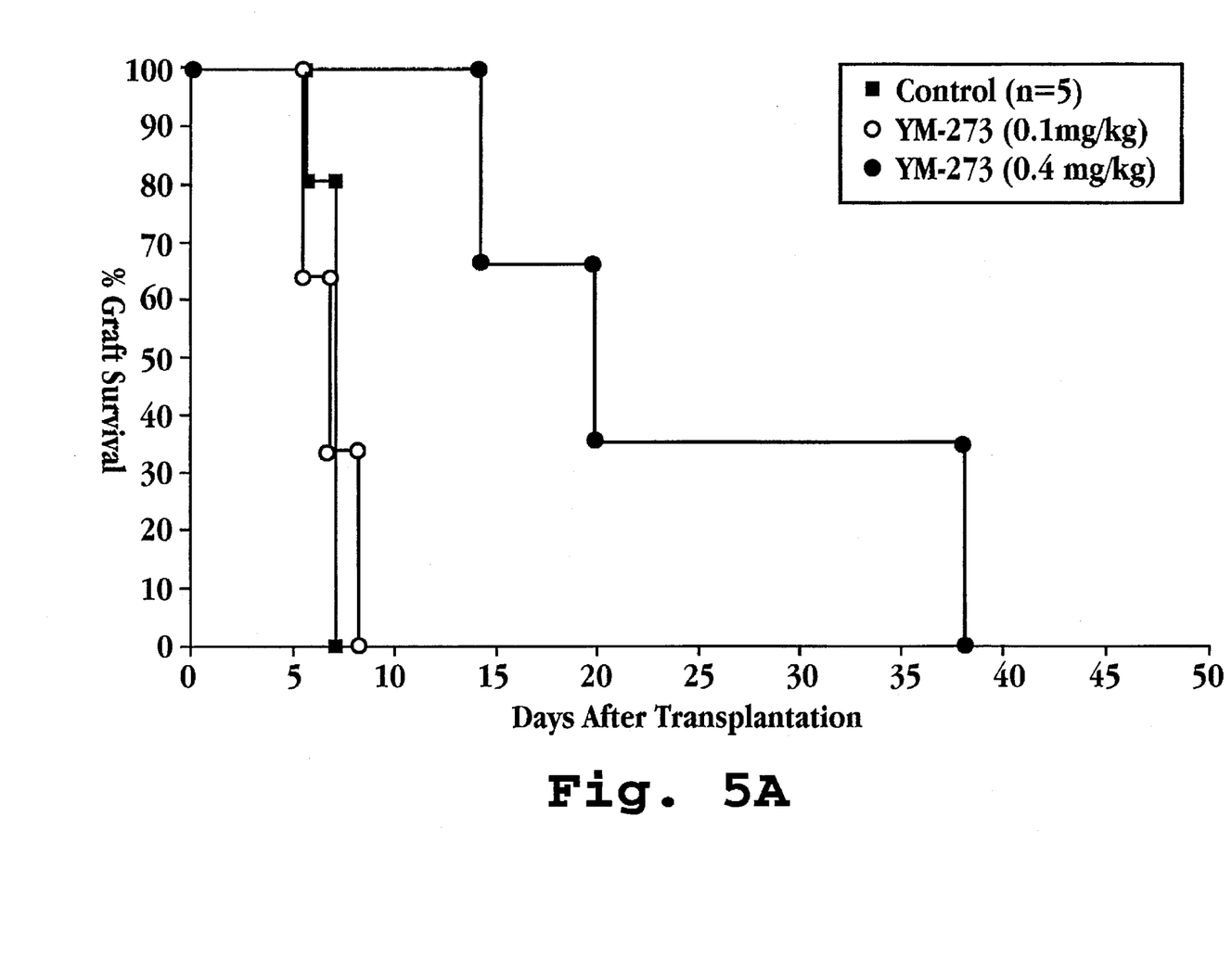
FIG. 5A shows a plot of allograft transplant survival time for untreated animals (closed squares), and animals treated with two different amounts of triptolide succinate tris (hydroxymethyl)aminomethane salt (YM-273) (open and closed circles)

As can be seen from FIG. 5A, YM-273 at a dosage level of 0.1 mg/kg (open circles) gave a mean survival time of 7 days, similar to the results obtained with the control group. However, a dosage of 0.4 mg/kg (closed circles) showed a substantial improvement over the control, with a mean survival time of 24 days.

Figure 5B:
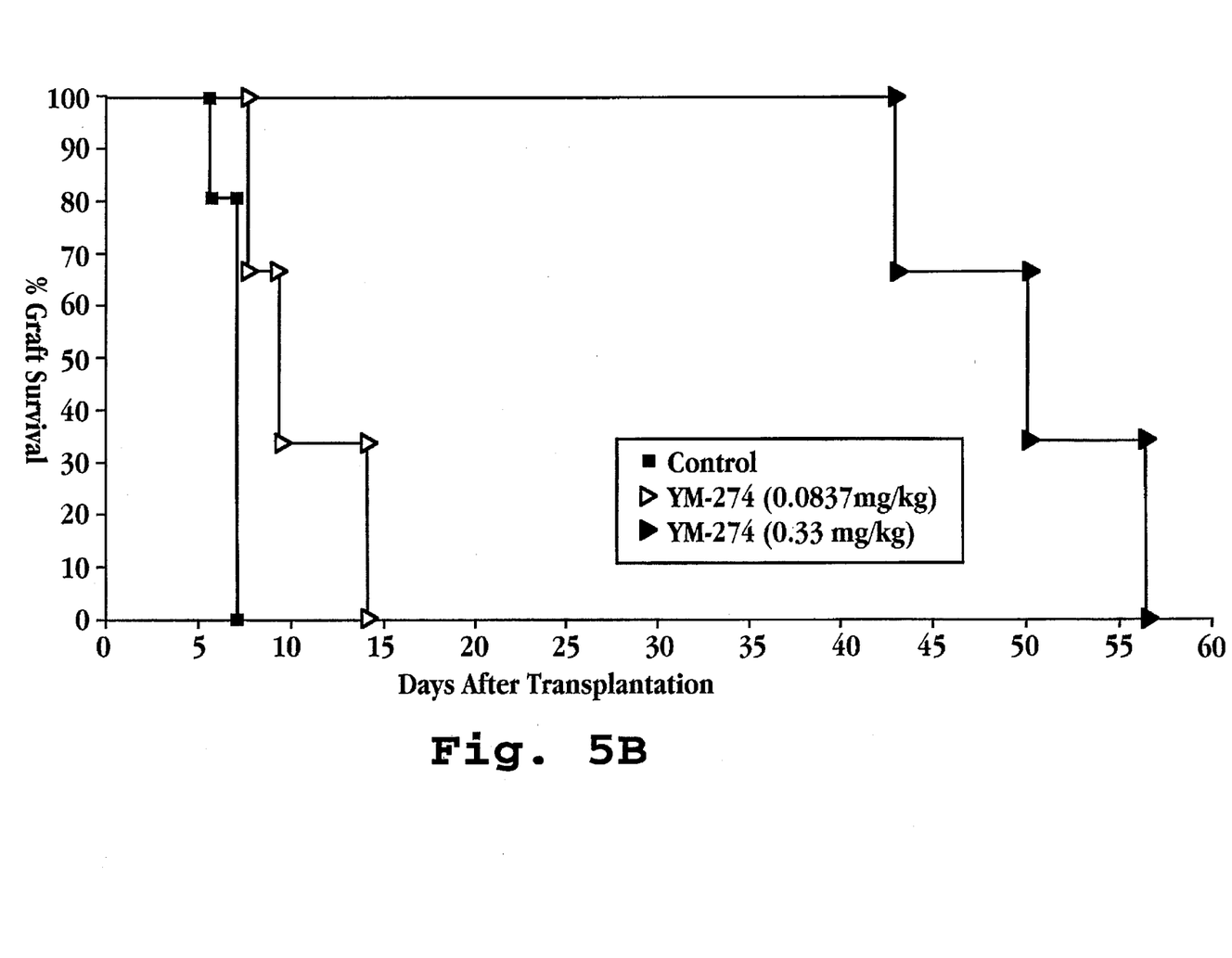
FIG. 5B shows a plot of allograft transplant survival time for untreated animals (closed squares), and animals treated with two different amounts of triptolide succinate sodium salt (YM-274) (open and closed triangles)

With reference to FIG. 5B, YM-274 administered at a dosage level of 0.0837 mg/kg (open triangles) gave a mean survival time of 10 days, whereas a dosage of 0.33 mg/kg (closed triangles) gave a mean survival time of approximately 50 days.

Figure 6:
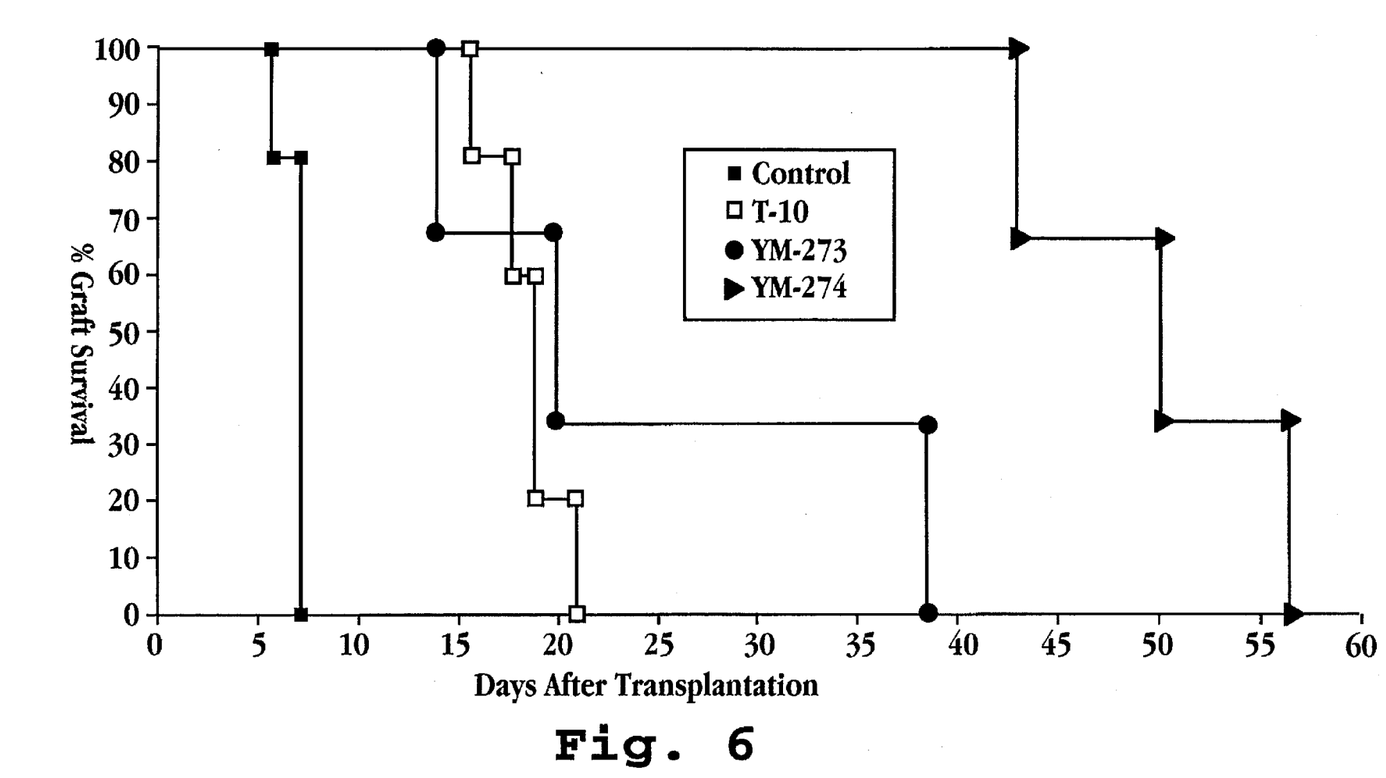
FIG. 6 shows a plot of allograft transplant survival time for untreated animals (closed squares), and for animals treated with triptolide (T10, open squares), triptolide succinate tris(hydroxymethyl)aminomethane salt (YM-273, closed circles), and triptolide succinate sodium salt (YM-274, closed triangles).

FIG. 6 compares the immunosuppressive effect of the higher doses of YM-273 and YM-274, described above, with equivalent doses (on a molar basis) of triptolide (T-10). As can be seen, the mean survival time obtained following administration of succinate derivatives YM-273 (tris salt) was somewhat better than that seen with underivatized triptolide, and was substantially better (50±7 days) in the case of succinate derivative YM-274 (sodium salt).

The above results indicate that the water soluble ester compounds of the invention have useful immunosuppressive activity in vivo, and that the compounds likely act as prodrugs, in that the ester groups are cleaved in vivo to produce the more active, underivatized triptolide compound.

V. Immunosuppressive Composition

Formulations containing the triptolide analogs of the invention may take the form of solid, semi-solid, lyophilized powder, or liquid dosage forms, such as, for example, tablets, pills, capsules, powders, sustained-release formulations, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the triptolide analog (about 0.5% to about 20%), and optional pharmaceutical adjuvants, in a carrier, such as, for example, aqueous saline, aqueous dextrose, glycerol, or ethanol, to form a solution or suspension.

The composition may be administered to a subject orally, transdermally or parenterally, e.g., by intravenous, subcutaneous, intraperitoneal, or intramuscular injection.

For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically usually used in the manufacture of medical preparations.

For parenteral administration, an injectable composition for parenteral administration will typically contain the triptolide analog in a suitable IV solution, such as sterile physiological salt solution. The high water solubility of the compounds of the invention make them particularly advantageous for administering in aqueous solution. The composition may also formulated as a suspension in a lipid (e.g., a triglyceride or a polyethoxylated castor oil such as "CREMOPHOR EL") or phospholipid, in a liposomal suspension, or in an aqueous emulsion.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable.

Compositions containing respirable dry particles of micronized active agent may be prepared by grinding dry active agent and passing the micronized composition through a 400 mesh screen to break up or separate out large agglomerates. The solid particulate form of the active agent may contain a dispersant to facilitate the formation of an aerosol. A suitable dispersant is lactose, which may be blended with the active agent in any suitable ratio (e.g., a 1:1 ratio by weight).

Any solid particulate medicament aerosol generator may be used to administer the solid particles. Such generators, such as the DeVilbiss nebulizer (DeVilbiss Co., Somerset, Pa.), produce particles which are respirable, as explained above, and generate a volume of aerosol containing a predetermined metered dose of a medicament at a rate suitable for human administration.

Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see *Remington's Pharmaceutical Sciences* (1980). The composition to be administered will contain a quantity of the selected compound in a pharmaceutically effective amount for effecting immunosuppression in a subject.

V. Treatment Method

The composition is employed in immunosuppression therapy, in particular, therapy in treating an autoimmune disease, graft-versus-host disease, or transplantation rejection. The composition is also useful for treatment of both intrinsic and extrinsic forms of asthma, and for treatment of other inflammatory conditions, such as traumatic inflammation.

Table III below gives a list of autoimmune diseases which are appropriate for immunotherapy.

TABLE III

| Autoimmune Diseases | |
|---|---|
| Disease | Tissue Affected |
| Addison's disease | adrenal |
| Allergies | inflammatory cells |
| Asthma | bronchi |
| Atherosclerosis | vessel walls |
| Chron's disease | intestine |
| Diabetes (Type I) | pancreas |
| Graves' disease | thyroid |
| Guillain-Barr´´Syndrome | nerve cells |
| Inflammatory bowel disease | intestine |
| Systemic Lupus erythematosis (SLE) | multiple tissues |
| Multiple sclerosis | nerve cells |
| Myasthenia Gravis | neuromuscular junction |
| Psoriasis | skin |
| Primary biliary cirrhosis | liver |
| Rheumatoid arthritis | joint lining |
| Uveitis | eye |

In treating an autoimmune condition, the patient is given the composition on a periodic basis, e.g., 1–2 times per week at a dosage level sufficient to reduce symptoms and improve patient comfort.

For treating rheumatoid arthritis, the composition may be administered by intravenous injection or by direct injection into the affected joint. The patient may be treated at repeated intervals of at least 24 hours, over a several week period following the onset of symptoms of the disease in the patient.

For the treatment of systemic lupus erythematosis (SLE), as another example, the composition may be administered by oral or parenteral administration, such as IV administration.

The dose that is administered is preferably in the range 1 to 25 mg/kg patient body weight per day, with lower amounts being preferred for parenteral administration, and higher amounts being preferred for oral administration. Parenteral administration may be by injection, e.g., intravenously, intramuscularly, or subcutaneously, inhalation, or uptake via a mucosal membrane.

For therapy in transplantation rejection, the method is intended particularly for the treatment of rejection of heart, kidney, liver, cellular, and bone marrow transplants. The method may also be used in the treatment of graft-versus-host disease, in which transplanted immune cells attack the allogeneic host. Initial treatment is administered perioperatively. In addition, the composition may be administered chronically to prevent graft rejection, or in treating acute episodes of late graft rejection. As above, the dose administered is preferably 1 to 25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogenic lymphocytes, or by taking a biopsy of the transplanted tissue.

In the treatment of asthma, intranasal administration (drops or spray), inhalation of an aerosol through the mouth, or conventional oral administration is generally preferred. The active agent may also be applied to the nasal respiratory epithelium as a topically applied liquid medicament. If the patient is unable to swallow, or oral absorption is otherwise impaired, the preferred systemic route of administration will be parenteral, intranasal, or topical.

The compounds of the invention may also be administered to an individual after onset of asthma to reduce breathing difficulty, or they may be administered prophylactically, that is, before the bronchospasm begins in an asthma attack, to prevent or minimize its occurrence.

The following examples are intended to illustrate but not in any way limit the invention.

EXAMPLE 1

Triptolide Succinate (YM-262)

Triptolide (100 mg) in 10 ml of pyridine was treated with succinic anhydride (150 mg) at room temperature. The reaction was carried out at 85° C. for 30 hours under a nitrogen atmosphere. Hexane (50 ml) was added to the resultant mixture to precipitate a crude product, which was collected by filtration and washed with hexane. The crude product was recrystallized from ether/hexane to yield 90 mg (70%) of triptolide succinate (YM-262), m.p. 111°–113° C.

IR(KBr): 3431.8, 2974.6, 1743.8, 1375.5, 1159.4, 1022.4 $cm^{-1}$. $H^1$NMR ($CDCl^3$): 5.08 (1H, s, 14-CH), 4.67 (2H, s, 19-CH2), 3.82 (1H, d, 11-CH), 3.50 (1H, d, 12-CH), 3.43 (1H, d, 7-CH), 2.75 (5H, m, CH2CH2, 5-CH), 2.30 (1H, d-m, 15-CH), 2.15 (2H, m, 6-$CH_a$, 2-$CH_a$), 1.88 (2H, m, 2-$CH_b$, 6-$CH_b$B), 1.55 (1H, m, 1-$CH_b$), 1.20 (1H, m, 1-CHa), 1.05 (3H, s, 20-CH3), 0.95 (3H, d, 16-$CH_3$), 0.83 (3H, d, 17-$CH_3$) ppm. MS (m/z): 461 (M+1).

EXAMPLE 2

Triptolide Succinate Tris Salt (YM-273)

Triptolide succinate (20 mg) was mixed with tris (hydroxymethyl)amino methane (5.3 mg) in 20 ml of water and stirred for one hour. The solution was filtered and the filtrate was lyophilized to yield 24 mg (96%) of white powder.

IR(KBr): 3391, 2937.96, 1745.80, 1562.9, 1411.67, 1159, 1066.57, 1024.57 cm$^{-1}$. H$^1$NMR (D$_6$-DMSO, ppm): 5.00 (1H, s, 14-CH), 4.85 (2H, d, 19-CH$_2$), 3.95 (1H, d, 11-CH), 3.70 (1H, d, 12-CH), 3.55 (1H, d, 7-CH), 3.30 (6H, s, 3CH$_2$O), 2.65 (1H, m, 5H), 2.45 (2H, m, CH2), 2.20 (3H, m, CH$_2$, 15-CH), 1.90 (4H, m, 6-CH2, 2-CH2), 1.34 (2H, br, 1-CH2), 0.95 (3H, s, 20-CH3), 0.88 (3H, d, 16-CH3), 0.75 (3H, d, 17-CH$_3$).

EXAMPLE 3

Triptolide Succinate Sodium Salt (YM-274)

Triptolide succinate (20 m9) was mixed with sodium bicarbonate (3.65 mg) in 20 ml of water and stirred for 30 min. The water solution was filtered and the filtrate was lyophilized to yield 20 mg (95%) white powder.

IR(KBr): 3431.8, 2975.56, 1743.87, 1577.97, 1419.79, 1163.22, 1022.40 cm$^{-1}$. H$^1$NMR (D6-DMSO, ppm): 5.00 (1H, s, 14-CH), 4.85 (2H, d, 19-CH2), 3.95 (1H, d, 11-CH), 3.70 (1H, d, 12-CH), 3.55 (1H, d, 7-CH), 2.58 (1H, m, 5H), 2.45 (2H, m, CH2), 2.20 (3H, m, CH2, 15-CH), 1.90 (4H, m, 6-CH2, 2-CH2), 1.34 (2H, br, 1-CH2), 0.95 (-3H, s, 20-CH3), 0.88 (3H, d, 16-CH3), 0.75 (3H, d, 17-CH3).

EXAMPLE 4

Triptolide Succinate Lysine Salt (YM-276)

Triptolide succinate (20 mg) mixed with L-(+)-lysine (6.3 mg) in 20 ml water was stirred for one hour. The solution was filtered and the filtrate was lyophilized to yield 25 mg (95%) white powder.

IR(KBr): 3431.8, 2934.0, 1743.9, 1560.6, 1399.9, 1147.6, 1018.6 cm$^{-1}$. H$^1$NMR (D$_6$-DMSO, ppm): 5.00 (1H, s, 14-CH), 4.85 (2H,d,19-CH$_2$), 3.95 (1H,d,11-CH), 3.78 (1H, d, 12-CH), 3.55 (1H, d, 7-CH), 3.50 (6H, br, 2NH$_3$), 3.15 (1H, m, —CH), 2.70 (1H, m, 5H), 2.65 (1H, m, CH$_2$), 2.4 (2H, m, CH$_2$), 2.20 (3H, m, CH$_2$, 15-CH), 1.90 (4H, m, 6-CH$_2$, 2-CH$_2$), 1.40 (6H, m, CH$_2$CH$_2$CH$_2$), 1.34 (2H, br, 1-CH$_2$), 0.95 (3H, s, 20-CH$_3$), 0.88 (3H, d, 16-CH$_3$), 0.75 (3H, d, 17-CH$_3$) ppm.

EXAMPLE 5

Synthesis of 14-N,N-Dimethylglycinate Ester of Triptolide

Into a dry 100 mL round bottom flask is placed 1 eq. of triptolide and 2 eq. each of N,N-dimethyl glycine and DCC (dicyclohexylcarbodiimide). The flask is placed under a nitrogen atmosphere, and anhydrous CH$_2$Cl$_2$ (dried over P$_2$O$_5$) is added, followed by a catalytic amount of DMAP (4-dimethylaminopyridine). The solution is stirred overnight at room temperature. The reaction is worked up by filtering off the dicyclohexylurea, removing the solvent by evaporation, and chromatographing the obtained solid on silica gel.

EXAMPLE 6

Synthesis of Methanesulfonic Acid Salt of 14-N,N-Dimethylglycinate Ester of Triptolide Into a dry round bottom flask is placed 1 eq. of the 14-N,N-dimethylglycinate ester of triptolide, as prepared in Example 5. The compound is dissolved in anhydrous C—H$_2$Cl$_2$ (distilled from P$_2$O$_5$), and to the resulting solution is added 1 eq. of a stock solution of methanesulfonic acid in diethyl ether. The solvent is immediately removed to yield a white solid.

EXAMPLE 7

Synthesis of 14-(3-(N,N-Dimethylamino) propionate) Hydrochloric Salt Ester of Triptolide Into a dry 100 mL round bottom flask is placed 1 eq. of triptolide and 2 eq. each of N,N-dimethylamino propionic acid and DCC (dicyclohexylcarbodiimide). The flask is placed under a nitrogen atmosphere, and anhydrous CH$_2$Cl$_2$ (dried over P$_2$O$_5$) is added, followed by a catalytic amount of DMAP (4-dimethylaminopyridine). The solution is stirred overnight at room temperature. The dicyclohexylurea is filtered off, and the solvent is removed by evaporation. The crude product is then chromatographed on silica gel.

EXAMPLE 8

Synthesis of 14-(4'-N-pyrrolidino)butyrate) Hydrochloride Salt Ester of Triptolide Into a dry round bottom flask is placed 1 eq. of triptolide, 2 eq. of 4-pyrrolidinobutyric acid hydrochloride salt, and anhydrous CH$_2$Cl$_2$ (distilled from P$_2$O$_5$). The resulting solution is placed under a nitrogen atmosphere, and 2 eq. of DCC and a catalytic amount of DMAP is added. The solution is stirred overnight at room temperature. The reaction is worked up by filtering off the dicyclohexylurea, removing the solvent by evaporation, and chromatographing the obtained solid on silica gel.

EXAMPLE 9

Synthesis of Bis N,N-Dimethylglycinate Ester of 16-Hydroxytriptolide

The title compound is synthesized by the reaction of 1 eq. of 16-hydroxytriptolide, 3 eq. of N,N-dimethylglycine, 3.3 eq. of DCC, and 0.16 eq. of DMAP in anhydrous CH$_2$Cl$_2$, followed by working up as described in the previous example.

The bis-N,N-dimethylglycinate ester at the 2- and 14-positions of triptolide is prepared in a similar fashion from tripdiolide (2-hydroxytriptolide).

EXAMPLE 10

Stability of Triptolide Succinate (YM-262)

A. Stability in Water

A solution of sodium triptolide succinate (YM-274) in D$_2$O was prepared at a concentration of 3 mg/ml and stored at room temperature. The solution was analyzed by $^1$H NMR at intervals of 1, 3, 5, 15, 45, 90, 180 minutes; 1, 7, 14 days; and 1, 2, 3, and 5 months. There was no appreciable change in the NMR spectrum during the first three months. Some decomposition was apparent after 5 months.

B. Stability in Blood Serum

A solution of triptolide succinate (free acid; YM-262) in DMSO was made at a concentration of 25 mg/ml, and 0.1 ml of this solution was mixed with 0.5 ml of rat serum. The mixture was incubated at 37° C. Aliquots of the mixture were taken at 1, 3, 5, 15, 45 minutes and 18 hours and analyzed by thin layer chromatography (TLC). The TLC plates were developed in 1:5 CH$_2$Cl$_2$/Et$_2$O. After development, the plates were treated with iodine vapor and examined under a UV lamp. Triptolide and triptolide succinate were used as reference compounds (R$_f$=0.60), and 0.45, respectively).

After 3 minutes, only triptolide succinate was detected by TLC. After 15 minutes, the triptolide succinate spot was gone ($R_f$=0.45), and a new spot corresponding to triptolide appeared ($R_f$=0.60). After 45 minutes, the triptolide spot also disappeared, and only low $R_f$ material (blood serum components and decomposition products) remained.

EXAMPLE 11

Inhibition of IL-1 Action on Murine Thymocytes

C3H/HeN mouse thymocytes were prepared and the action of IL-1 together with PHA, which stimulate proliferation of thymocyte, was measured using standard techniques (O'Gara, 1990; Mishell, 1980). Three- to six-week old C3H/HeN male mice (Simonson Laboratory, Gilroy, Calif.) were sacrificed by $CO_2$ inhalation. Thymi were removed, separated from adherent non-thymic tissue, homogenized in Hank's balanced salt solution (HBSS, Gibco) using a glass homogenizer, and centrifuged at 200×g for 10 minutes at 15° C. Following an additional wash in HBSS, the thymocytes were resuspended in RPMI 1640 medium containing 50 uM 2-mercaptoethanol, 2 mM glutamine, 1 mM sodium pyruvate, non-essential amino acids 100 U/ml penicillin, 100 µg/ml streptomycin, and 10% heat-inactivated fetal bovine serum.

Cells were cultured in round-bottom 96 well microtiter tissue culture plates, $6\times10^5$ cells per well, in a volume of 100 µl. Recombinant human IL-1β(R & D Systems #201-LB) together with Phytohemagglutinin P (PHA, Pharmacia) were added to the cells in volume of 25 µl per well to achieve a final concentration of 0.08 ng/ml and 10 µg/ml, respectively. Samples were dissolved in DMSO (10 mg/ml), then diluted in culture medium. Twenty five microliters of the test sample was added to each well to achieve the final compound concentrations for each experiment. Cells with PHA together with IL-1 served as controls. The total volume for each well was 150 µl.

Plates were incubated at 37° C. in a 5% $CO_2$ incubator for 72 hours. Fifty microliters of culture medium containing 0.5 µCi ($^3$H)-thymidine (Amersham, 49 Ci/mmol) was added to each well prior to the last 18 hours of incubation. Cells were then harvested and counted. The results were reported as counts per minute (cpm) per $6\times10^5$ cells.

The following formula was used to calculate the percent of suppression of IL-1 activity, and $IC_{50}$ (concentration of sample yielding 50% suppression of proliferation) was used to indicate the suppressive activity of the sample.

% suppression of IL-1 activity=(1-sample *cpm*/(IL-1+*PHA* control *cpm*)×100

The results are shown in Table I above.

EXAMPLE 12

Mixed Lymphocyte Reaction (MLR) Assay

In this study, the responder cells (R) were spleen cells from female C57BL/6 mice, and the stimulator cells (S) were spleen cells from female Balb/C mice 6 to 8 weeks of age (Jackson, Bar Harbor, Me). The spleens were aseptically removed from the mice and placed into 10 ml of cold HBSS in a sterile petri dish. The spleen was cut in half and gently pressed between the frosted ends of 2 sterile microslides. The cell suspension was then filtered through sterile nylon mesh (Nytex, Tetco #HD-3-85) into a 15 ml conical polypropylene centrifuge tube and centrifuged at 200×g for 10 minutes in a Beckman GPR tabletop centrifuge (GH-3.7 Rotor). Following an additional wash in HBSS, the spleen cells were resuspended in RPMI 1640 medium (Gibco) containing 50 uM 2-mercaptoethanol, 2 mM glutamine, 100 U/ml penicillin, 5 100 µg/ml streptomycin and 10% heat-inactivated fetal bovine serum.

The stimulator cells (S) and part of the responder cells (R) were diluted at $10\times10^6$ cells/ml and irradiated at 20 cGy with a Cesium Irradiator (Department of Radiation Oncology, Stanford University, Calif.) to inhibit proliferation. The irradiated cells were washed once to remove any toxic free radicals and their products resulting from irradiation. The responder cells (R), irradiated stimulator cells (Sx) and irradiated responder cell (Rx) were all diluted to $4\times10^6$ cells/ml.

In the assay, $4\times10^5$ cells of R were cocultured with $4\times10^5$ cells of Sx in 200 µl of medium in round bottom 96 well tissue culture plates. Fifty micro-liters of test samples at various concentrations were added to the cells. The wells receiving no test samples would get the maximum proliferation. Several controls were used in the assay. The irradiated responder cells (Rx) were also added to the responder cells with and without the test samples. Rx or Sx alone were checked to make sure no proliferation occurred after irradiation. The spontaneous proliferation of R was also measured.

The culture plates were incubated at 37° C. in a 5% $CO_2$ incubator for four days. The cells were labelled with 1 µCi of ($^3$H)-thymidine (Amersham, 49 Ci/mmol) in 20 µl of medium for the last 18 hours. Cells were then harvested and counted. The results were reported as counts per minute (cpm) per well. Percent of suppression and $IC_{50}$ (concentration of sample producing 50% suppression of proliferation) were used to indicate the suppressive activity of the sample. Sample cpm was calculated as (R+ Sx+sample)cpm−(R+Rx +sample)cpm; control cpm was calculated as (R+Sx)cpm−(R+Rx)cpm. Percent suppression of MLR activity was calculated as (1−sample cpm/control cpm)×100. $IC_{50}$ was determined from percent suppression to indicate the suppressive activity of the sample. The results are shown in Table II above.

EXAMPLE 13

Evaluation of Cytotoxicity

Potential cytotoxicity of the test samples was assessed by the measurement of their effect on the reduction of MTT (3-[4,5-Dimethylthiazole-2-yl]-2,5-diphenyltetrazolium bromide) by cultured cells. MTT, a yellow-colored compound, is reduced by mitochondrial enzymes to form the purple crystalline reduction product formazane, providing an index of cellular respiration on viable cells as well as a sensitive assay for cytotoxicity (Mossmann, 1983).

The cytotoxicity was assessed in cultured human PBMC and mouse thymocytes. A stock solution of MTT (Sigma) at 5 mg/ml in phosphate buffered saline, pH 7.4, was prepared and stored in the dark at 4° C. PBMCs or thymocytes were cultured with various concentrations of test samples in flatbottom 96-well tissue culture plates (Costar) under the same conditions as those described above, but the stimulants (X-35 or IL-1+PHA) were replaced by appropriate medium. Untreated cells with medium alone and without the test samples were used as controls. After incubation for 21 hours, 25 µl of MTT solution was added to each well. After an additional three hours of incubation, the experiment was terminated by addition of a solution of 10% sodium dodecyl sulfate in 0.01N HCl. Following overnight incubation at 37° C. to solubilize the formazane crystals, optical density was determined at 570–650 nm in microplate reader. The following formula was used to calculate % of toxicity:

% of toxicity=(1−sample *OD*/control *OD*)×100

Samples were defined as cytotoxic when toxicity was greater than 25% in the assay system used. The results are shown in Tables I and II above.

EXAMPLE 14

Treatment of Heart Transplant Rejection

Heterotopic whole heart transplantation was performed according to the standard method (Oho and Lindsey, 1969). The donors (Brown Norway rats, 200–255 g, Charles River, Wilmington, Mass.) and recipients (Adult male Lewis rats, 225–275 g, Charles River) were anesthetized with sodium pentobarbital (40 mg/kg). Following adequate donor anti-coagulation using heparin, the heart graft was removed and stored at 4° C. in PhysioSol Irrigation Solution (Abbott Laboratories, N. Chicago, Ill.). The ascending aorta and pulmonary artery were transected, and the vena cava and pulmonary veins were ligated. The recipient abdominal aorta and inferior vena cava were exposed through a median abdominal incision. The donor heart aorta and pulmonary artery were anastomosed end-to-side to recipient's infrarenal abdominal aorta and inferior vena cava, respectively, with running 8–0 monofilament nylon suture (Ethilon, Inc., Somerville, N.J.). Because of the functional properties of the aortic valve, blood did not enter the left ventricle but rather flowed through the coronary arteries to the right atrium, pulmonary artery and the recipient vena cava. The cold ischemic time of all the cardiac grafts was less than 45 minutes. Graft heartbeat was monitored by abdominal palpation. The period of functional graft survival was measured as the number of days during which cardiac graft contractions could be detected by abdominal palpation. Results were confirmed by direct visualization at laparotomy.

Heart transplant recipient animals prepared as described above (3–5 animals/group) were treated with (i) control solution (5% ethanol, 10 ml/kg), (ii) YM-273 at 0.10 mg/kg and 0.40 mg/kg (FIG. 5A), (iii) YM-274 at 0.084 and 0.33 mg/kg (FIG. 5B), and (iv) and T10 (triptolide) 0.25 mg/kg (FIG. 6). In addition to showing the results for T10, FIG. 6 repeats the results from FIGS. 5A–5B for YM-273 and YM-274 at 0.40 and 0.33 mg/kg, respectively, such that their concentrations were equimolar relative to T10. All compounds were administered intraperitoneally. Treatment started on the day prior to surgery and continuing daily until postoperative day 14, or until the end of allograft survival. Results are shown in FIGS. 5A–5B and 6.

While the invention has been described with reference to specific methods and embodiments, it will be appreciated that various modifications may be made without departing from the invention.

It is claimed:

1. A compound having the structure:

wherein $X^1$ is OH or $OR^1$, and $X^2$ and $x^3$ are independently OH, $OR^1$ or H, with the proviso that at least one of $X^1$, $X^2$ and $X^3$ is $OR^1$, and at least one of $X^2$ and $X^3$ is H; and $R^1$ is —C(O)—Y—Z, wherein Y is a branched or unbranched $C_1$–$C_6$ alkyl or alkenyl chain; and Z is $COOR^2$, $NR^3R^{3'}$, or $^+NR^4R^{4'}R^{4''}$, where $R^2$ is a cation;

$R^3$ and $R^{3'}$ are independently H or branched or unbranched $C_1$–$C_6$ alkyl, hydroxyalky, or alkoxyalkyl, or, $R^3$ and $R^{3'}$ taken together form a 5- to 7-member heterocyclic ring whose ring atoms are selected from the group consisting of carbon, nitrogen, oxygen, and sulfur, said ring including 2 to 6 carbon atoms and one or more nitrogen atoms; and $R^4$, $R^{4'}$, and $R^{4''}$ are independently branched or unbranched $C_1$–$C_6$ alkyl, hydroxyalkyl, or alkoxyalkyl.

2. The compound of claim 1, wherein $X^2=X^3=H$.
3. The compound of claim 1, where $X^2=H$.
4. The compound of claim 1, where $X^3=H$.
5. The compound of claim 1, wherein Z is COOH.
6. The compound of claim 1, wherein Z is $COOR^2$, and $R^2$ is a metal ion.
7. The compound of claim 6, wherein the metal ion is $Na^+$ or $K^+$.
8. The compound of claim 1, wherein Z is $COOR^2$, and $R^2$ is an organic amine.
9. The compound of claim 8, wherein the organic amine is lysine, triethylamine, or tris(hydroxymethyl) aminomethane.
10. The compound of claim 1, wherein Z is $NR^3R^{3'}$ and $R^3$ and $R^{3'}$ are independently H or branched or unbranched $C_1$–$C_6$ alkyl.
11. The compound of claim 1, wherein Z is $NR^3R^{3'}$ in protonated form or $^+NR^4R^{4'}R^{4''}$, and said compound includes an anionic counterion.
12. The compound of claim 11, wherein the anionic counterion is chloride or bromide.
13. The compound of claim 11, wherein the anionic counterion contains a carboxylate ion, sulfonate ion, or sulfate ion.
14. The compound of claim 11, wherein the anionic counterion is acetate, oxalate, maleate, fumarate, methanesulfonate, or toluenesulfonate.
15. The compound of claim 1, wherein Y is a $C_1$–$C_6$ alkyl chain, and Z is $COOR^2$.
16. The compound of claim 15, wherein $R^2$ is $Na^+$.
17. The compound of claim 16, wherein $R^2$ is tris(hydroxymethyl)ammonium methane or lysine.
18. The compound of claim 1, wherein Y is a $C_1$–$C_4$ alkyl chain, and Z is dimethyl amino.
19. The compound of claim 1, wherein Y is a $C_1$–$C_4$ alkyl chain, and Z is N-morpholino.

* * * * *